(12) United States Patent
Graham

(10) Patent No.: US 9,604,027 B2
(45) Date of Patent: Mar. 28, 2017

(54) GAS-TREATMENT DEVICES

(71) Applicant: SMITHS GROUP PLC, London (GB)

(72) Inventor: Mark Andrew Graham, Kent (GB)

(73) Assignee: SMITHS GROUP PLC, London (GB)

( * ) Notice: Subject to any disclaimer, the term of this patent is extended or adjusted under 35 U.S.C. 154(b) by 0 days.

(21) Appl. No.: 14/874,556

(22) Filed: Oct. 5, 2015

(65) Prior Publication Data

US 2016/0082219 A1    Mar. 24, 2016

Related U.S. Application Data

(62) Division of application No. 11/793,235, filed as application No. PCT/GB2005/005067 on Dec. 23, 2005, now abandoned.

(30) Foreign Application Priority Data

Jan. 6, 2005 (GB) .................................. 0500133.4
Jan. 29, 2005 (GB) .................................. 0501937.7

(51) Int. Cl.
*A61M 16/10* (2006.01)
*A61M 16/04* (2006.01)
*A61M 16/08* (2006.01)

(52) U.S. Cl.
CPC ...... *A61M 16/1045* (2013.01); *A61M 16/047* (2013.01); *A61M 16/0816* (2013.01); *A61M 16/0875* (2013.01); *A61M 2202/0208* (2013.01)

(58) Field of Classification Search
CPC .............. A61M 16/1045; A61M 16/16; A61M 16/047; A61M 16/0816; A61M 16/0875; A61M 2202/0208
See application file for complete search history.

(56) References Cited

U.S. PATENT DOCUMENTS

| | | | |
|---|---|---|---|
| 3,881,482 | A | 5/1975 | Lindholm |
| 4,456,007 | A | 6/1984 | Nakao et al. |
| 4,971,054 | A | 11/1990 | Andersson et al. |
| 5,109,471 | A | 4/1992 | Lang |
| 5,186,164 | A | 2/1993 | Raghuprasad |
| 5,505,768 | A | 4/1996 | Altadonna |
| 6,158,431 | A | 12/2000 | Poole |

(Continued)

FOREIGN PATENT DOCUMENTS

| | | |
|---|---|---|
| DE | 20114355 | 12/2001 |
| DE | 20302580 | 4/2003 |

(Continued)

OTHER PUBLICATIONS

PCT International Search Report and Written Opinion (PCT/GB2005/005067), ISA: EPO; mailed Feb. 24, 2006.

*Primary Examiner* — LaToya M Louis
(74) *Attorney, Agent, or Firm* — Louis Woo

(57) ABSTRACT

An HME has exchange elements (4) at opposite ends of a tubular housing (1, 101) and a central port (2) for connection to a tracheal tube (3). An oxygen port (5, 105, 105') is located centrally with the major part of it being contained within a recess (40, 140, 140') on the exterior of the housing and extending at right angles to the length of the housing. The oxygen port (5, 105, 105') opens into a wider passage (32, 32') extending within the housing, which opens on the external face (30) of the two exchange elements (4). A large suction aperture (60) aligns with the port (2) opening to the tracheal tube (3) and is covered by a hinged flap (61) when not in use.

8 Claims, 4 Drawing Sheets

(56) References Cited

U.S. PATENT DOCUMENTS

| | | |
|---|---|---|
| 6,363,930 B1 | 4/2002 | Clawson et al. |
| 6,422,235 B1 | 7/2002 | Persson |
| 6,550,476 B1 | 4/2003 | Ryder |
| 2002/0157667 A1 | 10/2002 | Fini |
| 2005/0188990 A1 | 9/2005 | Fukunaga et al. |

FOREIGN PATENT DOCUMENTS

| | | |
|---|---|---|
| EP | 1208866 | 5/2002 |
| GB | 2391816 | 2/2004 |
| SE | 516666 | 2/2002 |
| WO | WO 97/01366 | 1/1997 |
| WO | WO 01/72365 | 10/2001 |

GAS-TREATMENT DEVICES

FIELD OF THE INVENTION

This invention relates to gas-treatment devices of the kind having a housing, a first port adapted for connection to a patient breathing device, a gas-treatment element through which gas can flow in both directions to and from the patient and a second, oxygen supply port by which oxygen can be supplied to the patient via the gas-treatment device, the oxygen supply port being in the form of a tubular stem.

BACKGROUND OF THE INVENTION

The invention is more particularly, but not exclusively, concerned with heat and moisture exchangers (HMEs) of the kind connected to a patient breathing device.

Where a patient breathes through a tube inserted in the trachea, such as a tracheostomy or endotracheal tube, gas flow to the bronchi is not warmed and moistened by passage through the nose. Unless the gas is warmed and moistened in some way it can cause damage and discomfort in the patient's throat. The gas can be conditioned by a humidifier in the ventilation circuit but, most conveniently, a heat and moisture exchange device (HME) is used. HMEs are small, lightweight devices including one or more exchange elements, such as of a paper or foam treated with a hygroscopic substance. When the patient exhales, gas passes through the exchange element and gives up a major part of its heat and moisture to the element. When the patient inhales, gas passes through the exchange element in the opposite direction and takes up a major part of the heat and moisture in the exchange element so that the gas inhaled by the patient is warmed and moistened. These HMEs are low cost and disposable after a single use so do not require cleaning or present any cross contamination risk. They can be connected in a breathing circuit or simply connected to the machine end of a tracheal tube and left open to atmosphere where the patient is breathing spontaneously.

HMEs are sold by Smiths Medical International Limited of Hythe, Kent, England under the Thermovent name (Thermovent is a registered trade mark of Smiths Medical International Limited), by Hudson RCI AB under the TrachVent name (TrachVent is a registered trade mark of Hudson RCI AB), by DAR, Medisize, Intersurgical and other manufacturers. HMEs often include an oxygen inlet port to which an oxygen supply tube can be connected. This enables supplementary oxygen to be administered to the patient via the HME. Advantageously, the oxygen port opens on the side of the HME element remote from the patient so that the oxygen has to pass through the HME element before reaching the patient. Examples of HMEs with oxygen supply ports are described in GB 2391816, WO 01/72365, U.S. Pat. No. 5,505,768, SE 516666, U.S. Pat. No. 3,881,482, DE 20302580, DE 20114355U, WO 97/01366, US 2002/0157667, U.S. Pat. No. 6,422,235, EP 1208866 and U.S. Pat. No. 4,971,054.

Because the HME is often connected to the end of a tracheal tube it is desirable that its construction be as compact as possible.

SUMMARY OF THE INVENTION

It is an object of the present invention to provide an alternative gas-treatment device.

According to one aspect of the present invention there is provided a gas-treatment device of the above-specified kind, characterised in that the housing has a recess on its external surface, and that the major part of the oxygen supply port extends within the recess when not in use.

The device preferably has two gas-treatment elements at opposite ends of the housing. The oxygen supply port may be located intermediate the ends of the housing. The or each gas-treatment element may be an HME exchange element. The housing preferably has an elongate shape and the port preferably extends at right angles to the axis of the housing. The oxygen supply port may be displaceable from a first position in which a major part of the port is contained within the recess and a second position in which it projects from the recess for connection of an oxygen supply tube. The port may be displaceable by rotation or by sliding. The housing may have a suction aperture located substantially opposite the first port, the suction aperture being covered by a flap that can be displaced to enable a suction catheter to be extended through the suction aperture into the patient breathing device. An oxygen supply passage preferably extends along the housing and opens onto an external face of the or each gas-treatment element, the oxygen supply port being directed at an angle to the oxygen supply passage such that oxygen flow changes direction where it emerges from the port into the passage, and the cross-sectional area of the oxygen passage being greater than that of the oxygen port so that oxygen pressure drops where it emerges from the port into the passage.

BRIEF DESCRIPTION OF THE FIGURES

An HME according to the present invention will now be described, by way of example, with reference to the accompanying drawings, in which.

Figure 1:
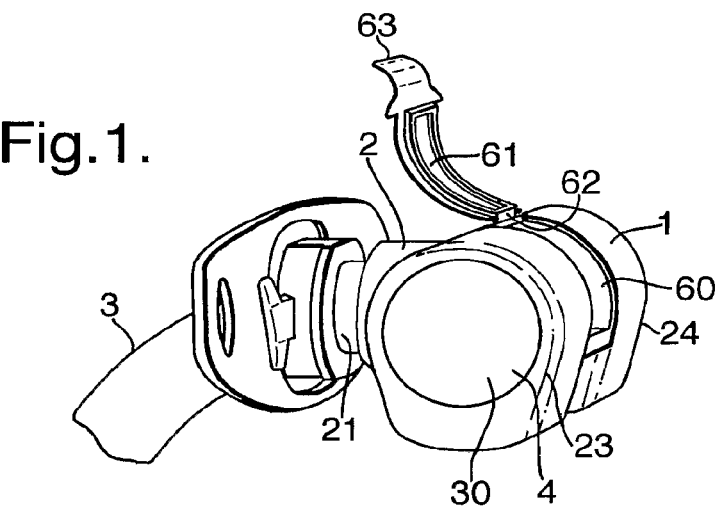
FIG. 1 is a perspective side view of the HME connected to the end of a tracheostomy tube.
Figure 2:
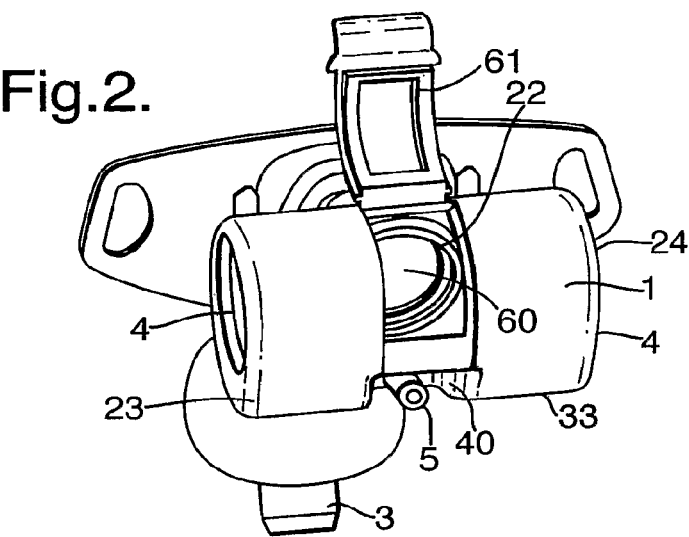
FIG. 2 is a perspective end view of the HME.
Figure 3:
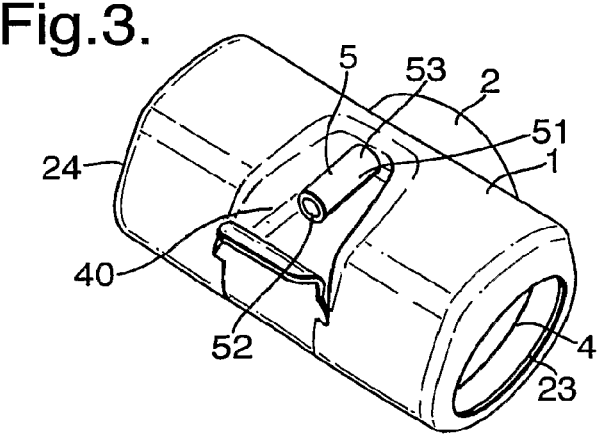
FIG. 3 is view of the lower side of the HME.
Figure 4:
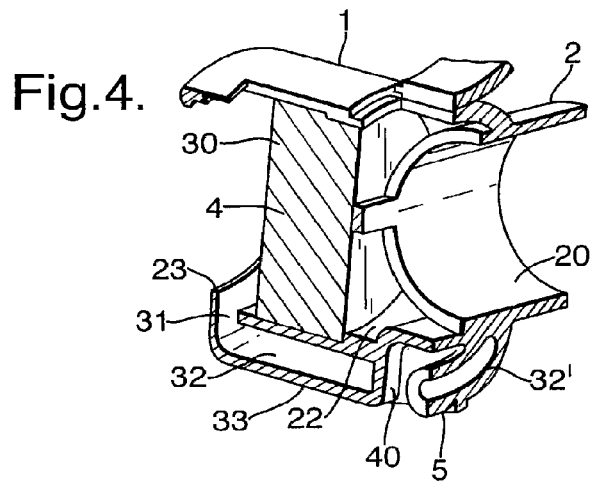
FIG. 4 is a cross-sectional view of a part of the HME.

With reference first to FIGS. 1 to 4, the HME has an outer housing 1 with a coupling or port 2 by which it is connected to a tracheal tube 3. The housing 1 supports two heat and moisture exchange elements 4 at opposite ends by which gas supplied to the patient is warmed and moistened. An oxygen supply port 5 is mounted on the housing 1 to enable supplementary oxygen to be supplied to the patient when necessary.

The housing 1 is generally cylindrical and is moulded from a rigid plastics material. The patient coupling 2 projects radially outwardly of the housing midway along its length and has an internal tapered surface 20 adapted to connect to a standard male tapered coupling 21 on the end of the tracheal tube 3. The coupling 2 opens to the interior 22 of the housing 1 in communication with the inner surface of the exchange elements 4.

The exchange elements 4 are each conventional, being in the form of a disc comprising a spiral roll of corrugated paper treated with a hygroscopic salt to promote the retention of moisture. The exchange elements 4 extend transversely of the axis of the housing 1, being retained on the ends of the housing by annular, inwardly-projecting end flanges 23 and 24. The external face 30 of each exchange element 4 is located just rearwardly of a curved slot 31 formed between the end of the housing 1 and the respective end flanges 23 and 24. Each slot 31 communicates with an oxygen conduit 32 extending longitudinally of the HME in a ridge 33 along the lower side of the housing 1. The space between the external face 30 of the exchange elements 4 and the ends of the housing 1 helps protect the elements from contact and contamination.

Midway along its length, the ridge 33 is interrupted by a recess 40, of a tapering shape, on the lower side of the exterior of the housing 1. The depth of the recess 40 is about half the width of the ridge 33, the oxygen conduit 32 continuing with a reduced width behind the recess, along the entire length of the housing 1 so that the slots 31 at both ends communicate with one another via the conduit. The recess 40 serves to house and protect the oxygen supply port 5.

The oxygen supply port 5 is formed by a stem 51 of circular external section and with a taper on its external surface such that its outer, free end 52 has a smaller diameter than its inner end 53. The port 5 extends parallel to the patient coupling 2 in the opposite direction, that is, at right angles to the axis of the housing 1. The oxygen supply port 5 is located in the recess 40 on the lower side of the housing and its length is such that it is entirely contained within the recess. In modifications of the HME, the oxygen supply port could project slightly from the recess providing that the major part of its length was contained within the recess. The space within the recess 40 around the oxygen supply port 5 is such as to enable a female coupling on the end of an oxygen supply tube (not shown) to be pushed onto and retained on the port.

Oxygen supplied to the port 5 flows through the relatively narrow passage through the port and opens into the section 32' of the oxygen conduit 32. This space 32' has a larger cross-sectional area (typically about 13.4 mm.sup.2) than that of the passage through the oxygen port (typically about 3.1 mm.sup.2) thereby resulting in a drop in pressure as the oxygen flows out of the port 5 into the section 32'. The flow of oxygen is then abruptly diverted through 90.degree. as it flows outwardly in both directions away from the port 5. This change in direction produces turbulence and a further drop in pressure. The oxygen then flows from the reduced width section 32' into opposite ends of the main section 32 and, because these have a larger cross-sectional area (typically about 47.9 mm.sup.2) than the reduced width section, this results in a further reduction in the pressure of the oxygen. Oxygen flow from the port 5 in both directions is substantially equal because of the central location of the port and its symmetrical disposition. Oxygen flows along the conduit 32 and out of the slots 31 over the external surface 30 of the two exchange elements 4. In this way, the supplementary oxygen has to pass through the exchange elements 4 before passing to the trachea, so that it is warmed and moistened in the same way as the ambient air. The reduced pressure caused by the geometry of the oxygen flow path from the port 5 to the external surfaces of the exchange elements 4 reduces the flow rate out of the slots 31 and ensures that a maximum proportion of the oxygen remains in the region of the exchange elements without flowing past them. This helps ensure the maximum efficiency of oxygen mixing with ambient air in the region of the exchange elements 4 and hence the maximum concentration of oxygen supplied to the patient.

The HME additionally has a suction access aperture 60 located directly opposite the tracheal tube coupling 2. The aperture 60 is rectangular and is normally covered and closed by a cover or flap 61 formed integrally with the housing 1 and attached with it at one end by a web or living hinge 62, which is bendable to allow the flap to be raised or lowered over the aperture. The edges of the flap 61 and the aperture 60 are shaped such that the flap can snap into position in the aperture and provide a substantially gas-tight seal. The free end 63 of the flap 61 is curved away from the surface of the housing 1 to form a lip when the flap is closed by which it can be gripped and opened. When the patient's tracheal tube 3 needs suctioning, the clinician lifts the flap 61 and inserts the suction tube down the tracheal tube through the patient coupling 2. This avoids the need to remove the HME. The fit of the flap 61 in the aperture 60 could be arranged such that the flap can be blown outwardly by increased pressure created by the patient, such as when coughing. This would provide a pressure relief feature. The dimensions of the suction aperture 60 are relatively large so that a suction catheter can be inserted through the aperture with minimal contact with the edge of the aperture so as to minimize wiping the catheter and thereby reduce the risk that secretions on the outside of the catheter will be removed and remain inside the HME. Preferably the width of the aperture 60 is at least substantially the same as the internal diameter of the tracheal tube 3 with which the HME is used, typically the width is about 10 mm and the depth is about 16 mm. Suction catheters should have an external diameter not greater than half the internal diameter of the tracheal tube, the maximum size of the suction catheter usually being 16 F, that is 5.3 mm outside diameter, for use with a 10 mm internal diameter tracheal tube.

By locating the oxygen supply port in a recess where it is contained substantially entirely within the boundaries of the recess, in the manner described above, the HME can present a compact configuration and its surface is less likely to snag on adjacent tubes, dressings, wires or the like when not in use.

The oxygen supply port need not be concealed within the recess when connected to the oxygen supply tube. Instead, the port could be displaceable from a position where it is concealed within a recess, when not in use, to a position where it projects from the recess, when in use.

In the arrangement shown in FIGS. 5 to 8, the oxygen supply port 105 has an outer tapered portion 106 and a shorted, inner stem 107 projecting at right angles to the outer portion. As most clearly shown in FIG. 8, the stem 107 is solid and formed with a bifurcated toothed end 108, which is a snap fit in a hole 109 through the upper wall 110 of the recess 140 into the interior 122 of the housing 101. One side of the stem 107 makes close sliding contact in a concave cavity 146 formed in the corner between a rear wall 147 and a side wall 148 of the recess 140 adjacent the hole 109. The cavity 146 has a small opening 149 located towards the rear wall 147 and opening through the wall into the conduit 132.

Figure 5:
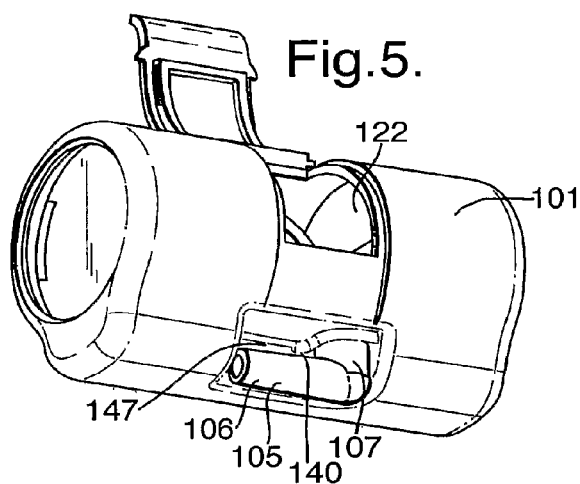
FIG. 5 is a perspective view of an alternative HME with its oxygen port stowed.

A passage 152 extends axially through the outer portion 106 of the port 105 from the open, forward end 151 to a rear opening 153 formed in the wall of the stem 141. The oxygen supply port 105 is rotatable through 90.degree. about the axis of the stem 107, the fit of the toothed end 108 in the hole 109 enabling the stem to rotate in the hole, whilst the friction between the stem and the hole is sufficient to ensure that the port remains in whatever angular position to which it is displaced. In the stowed position shown in FIG. 5, the outer portion 106 extends parallel to the axis of the housing 101 and parallel to its external surface, alongside the rear wall 147 of the recess 140. The length of the outer portion 106 locates in the recess 140 with just a small part of its width protruding so that the major part of the port 105 is contained within the boundaries of the recess. In this position, the curved surface of the stem 107 blocks any flow of gas through the opening 149. When the oxygen supply port 105 is stowed, as shown in FIG. 5, the external surface of the HME is substantially uninterrupted by projections so that it presents a compact, retracted configuration.

Figure 6:
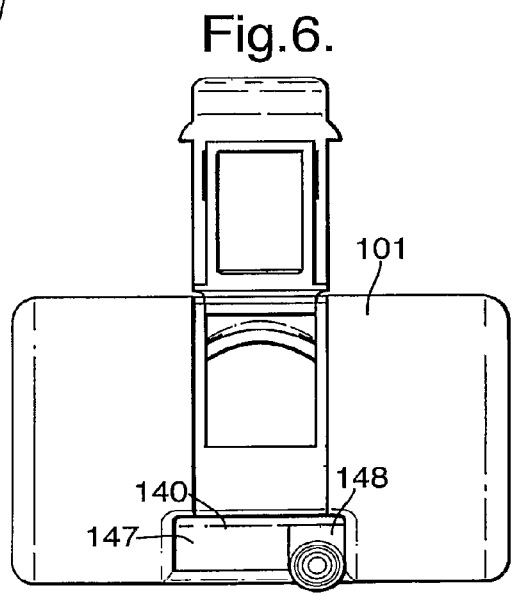
FIG. 6 is a side elevation view of the HME of FIG. 5 with the oxygen port extended.
Figure 7:
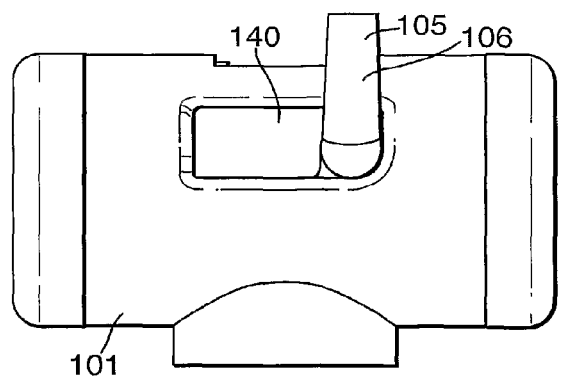
FIG. 7 is a view of the underside of the HME of FIG. 5 with the oxygen port extended.
Figure 8:
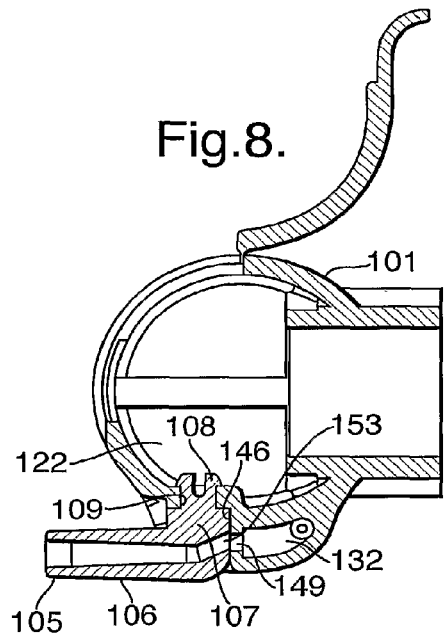
FIG. 8 is a cross-sectional view of the HME with the oxygen port extended.

When the oxygen supply port 105 is swung clockwise through 90.degree. (as viewed from below and as shown in FIGS. 6, 7 and 8) the outer portion 106 extends outwardly at right angles to the axis of the housing 101 so that the oxygen supply tubing can be connected to it readily. In this position, the rear opening 153 of the oxygen supply port 105 aligns with the opening 149 so that oxygen can flow along conduit 132.

Figure 9:
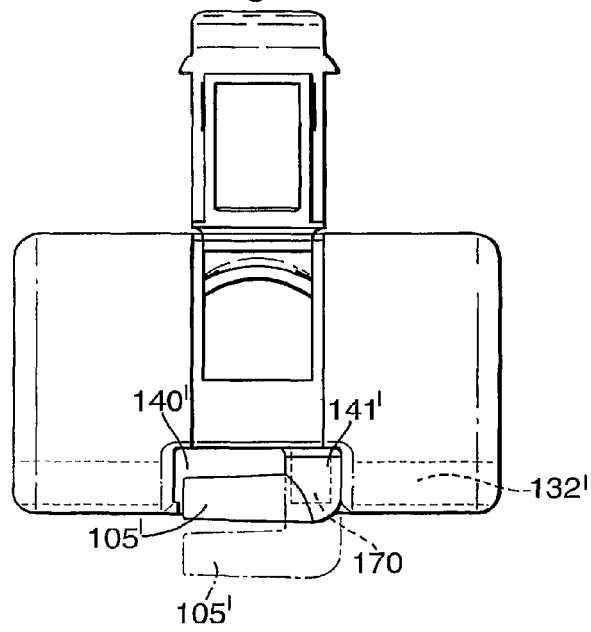
FIG. 9 is a side elevation view of a second alternative, modified HME.

It is not essential for the oxygen supply port be displaceable between an extended and retracted position by rotation. As shown in FIG. 9, the port 105' could be movable linearly in a slidable, telescopic fashion. In this arrangement, the port 105' has an inner stem 141' slidably mounted in a telescopic fashion on the outside of a short, radially extending tube 170 opening into the conduit 132'. The outer stem 142' extends at right angles to the inner stem 141' in the same manner as in the swivel port 105. The telescopic movement is such that, in its retracted position, substantially all the port 105' is contained within the boundaries of the recess 140' whereas, when pulled out fully to its extended position, the outer stem 142' extends outside the recess 140' so that an oxygen supply connector can be fitted easily to the stem. The mounting of the inner stem 141' on tube 170 could be such as either to prevent or to permit rotation of the port 105'. Where rotation is prevented, the outer stem 142' would be confined to extend only parallel to the axis of the HME. Where rotation is permitted, the outer stem 142' would be free to swivel to any desired orientation once pulled out of the recess 140'. Because rotation of the port 105' is not hindered by contact with the sides of the recess 140', when it is extended, it can be free to rotate through 360.degree. The port 105' could be arranged to restrict flow of gas through it when in the retracted position. This could be achieved by means of a formation inside the port 105' that obstructs the end of the tube 170 when the port is retracted. Alternatively, the open end of the outer stem 142' could be arranged to be obstructed by a formation on the inside of the recess 140' when in its stowed, retracted position. Instead of the inner stem 141' embracing the outside of the tube 170, alternative arrangements could have an inner stem extending inside a tube in a telescopic fashion. The port need not be bent at an angle but could simply be straight, aligned with the axis of telescoping movement. In such an arrangement, it might be desirable for the port to be able to be locked in its extended position so as to facilitate coupling to the oxygen tubing. This could be achieved by a pull-and-twist bayonet action. After use, the port would be unlocked and retracted to its stowed position within a recess.

Figure 10:
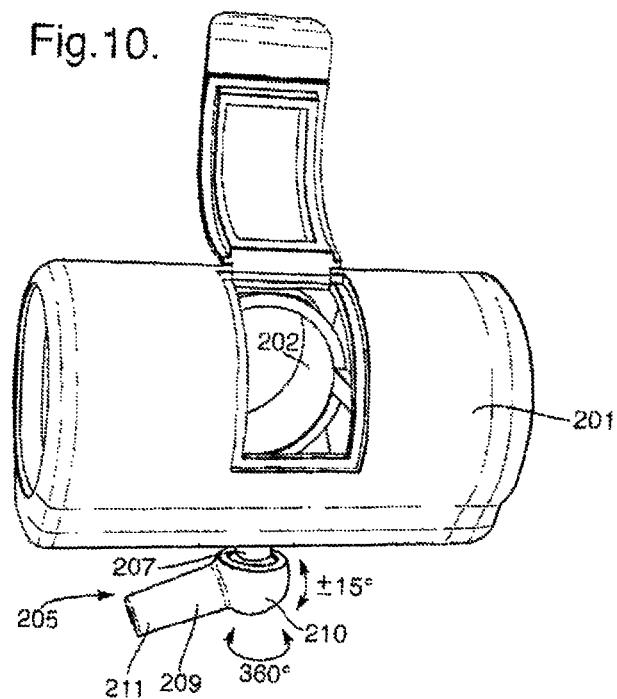
FIG. 10 is a perspective view of a third alternative HME.
Figure 11:
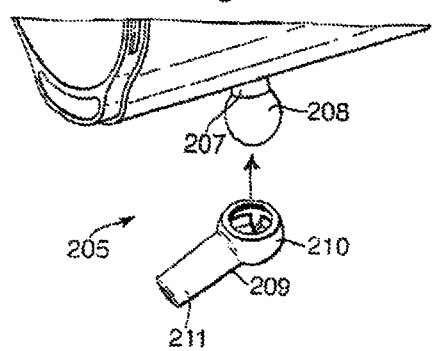
FIG. 11 shows a part of the HME of FIG. 10 with components separated.

A further alternative arrangement is shown in FIGS. 10 and 11 where the oxygen supply port 205 is of a two-part ball and socket construction. A spigot 207 projects downwardly from the housing 201 at right angles to the axis of the patient port 202 and is terminated by an enlarged ball formation 208. A separate arm 209 comprising a cup or socket 210 has an externally tapered stem 211 angled downwardly relative to the flat end surface of the socket by about 30°. The arm 209 can be rotated about the axis of the spigot 207 by 360° to any desired position. The stem 211 can also be angled up or down by 15° so that the stem can take any angle between 15° and 45° relative to the axis of the housing 201. Friction between the ball 208 and socket 210 ensures that the arm 209 remains in the position to which it is set.

It will be appreciated that the invention is not confined to HMEs but could be used with other devices such as where the gas-treatment elements are filters.

The invention claimed is:

1. A HME (Heat and Moisture Exchanger) comprising: a housing having a length extending along an axis, a first port projects from the housing adapted for connection to a patient breathing device, a HME element extends transversely of the axis at opposite ends of the housing through which gas can flow to and from a patient, a recess provided at a lower side and midway along the length of the housing, an oxygen supply port by which oxygen can be supplied to the patient via the HME, the oxygen supply port having a stem with an inner end attached to a wall of the recess and a free open end adapted to physically attach to an oxygen line, the oxygen supply port having at least a major part of the stem contained within the recess when not in use, an oxygen passage extending along the housing to connect with the stem, a suction aperture located substantially opposite the first port, and a flap having one end hingedly attached to the housing being movable to cover the suction aperture and an opposite, free end that extends over a part of the recess to cover the major part and to cover and face the free open end of the stem.

2. The HME of claim 1, wherein the oxygen supply port extends parallel to the first port in an opposite direction.

3. The HME according to claim 1, wherein the flap is movable to uncover the suction port so that a suction catheter can be extended through the suction aperture into the patient breathing device.

4. The HME according to claim 1, wherein when covering the suction aperture, the flap is arranged to provide a substantially gas-tight seal fit for the suction aperture, the fit to the suction aperture being arranged such that the flap is blown away from the suction aperture due to an increased pressure in the housing.

5. The HME according to claim 1, wherein the HME element is an HME exchange element.

6. The HME according to claim 1, wherein the oxygen passage extends along the housing to open onto an external face of the HME element, the oxygen supply port being directed at an angle to the oxygen supply passage such that oxygen flow changes direction where it emerges from the port into the passage, and wherein a cross-sectional area of the oxygen passage is greater than a cross-sectional area of the oxygen port so that oxygen pressure drops where it emerges from the port into the passage.

7. The HME according to claim 1, wherein the oxygen supply port is located at right angles to the axis of the housing and is entirely contained within the recess.

8. A HME (Heat and Moisture Exchanger) having a housing having a longitudinal axis, a first port extending from the housing at right angles to the longitudinal axis and substantially midway along a length of the housing, the first port being adapted for connection to a patient breathing device, a HME element at opposite ends of the housing through which gas can flow to and from the patient, a second oxygen supply port in the form of a tubular stem extending substantially parallel to the first port and at right angles to the longitudinal axis of the housing, the second port being arranged to supply oxygen to the patient via the HME, wherein the housing has a recess provided at a lower side and midway along the length of the housing, wherein a major part of the oxygen supply port extends within the recess, the tubular stem of the oxygen supply port having an inner end attached to a wall of the recess and a free open end adapted to physically attach to an oxygen line; wherein the housing includes a suction aperture located substantially opposite the first port, wherein the device includes a flap that is hinged at one end on the housing and covers the suction aperture, and wherein the flap has an opposite, free end extending over a part of the recess and covering and facing the open free end of the tubular stem, the flap being displaceable about its hinged end to reveal the suction aperture and enable a suction catheter to be extended through the suction aperture into the patient breathing device.

* * * * *